United States Patent [19]

Longo

[11] Patent Number: 5,660,934
[45] Date of Patent: Aug. 26, 1997

[54] CLAD PLASTIC PARTICLES SUITABLE FOR THERMAL SPRAYING

[75] Inventor: Frank N. Longo, East Northport, N.Y.

[73] Assignee: Spray-Tech, Inc., Newtown, Conn.

[21] Appl. No.: 366,260

[22] Filed: Dec. 29, 1994

[51] Int. Cl.$^6$ .................................................. B32B 5/16
[52] U.S. Cl. ............... 428/404; 428/407; 428/698; 428/699; 428/701; 428/702; 428/704; 428/570
[58] Field of Search .................................. 428/403, 404, 428/407, 413, 421, 422, 473.5, 474.4, 477.7, 458, 461, 469, 472, 480, 539.5, 698, 699, 701, 702, 704, 570; 75/346, 255, 252, 351, 342, 230

[56] References Cited

U.S. PATENT DOCUMENTS

| | | | |
|---|---|---|---|
| 3,305,326 | 2/1967 | Longo | 29/192 |
| 3,313,633 | 4/1967 | Longo | 106/1 |
| 3,338,688 | 8/1967 | Longo | 29/192 |
| 3,607,343 | 9/1971 | Longo et al. | 117/27 |
| 3,655,425 | 4/1972 | Longo et al. | 117/100 |
| 3,723,165 | 3/1973 | Longo et al. | 117/93.1 PF |
| 3,991,240 | 11/1976 | Harrington et al. | 427/423 |
| 4,388,373 | 6/1983 | Longo et al. | 428/413 |
| 4,450,184 | 5/1984 | Longo et al. | 427/34 |
| 4,694,990 | 9/1987 | Karlsson et al. | 239/81 |
| 4,741,974 | 5/1988 | Longo et al. | 428/558 |
| 4,743,940 | 5/1988 | Nagasaka et al. | 355/3 |
| 5,196,471 | 3/1993 | Rangaswamy et al. | 524/406 |
| 5,292,382 | 3/1994 | Longo | 148/320 |

FOREIGN PATENT DOCUMENTS

| | | | |
|---|---|---|---|
| 0379995 | 8/1990 | European Pat. Off. | C23C 4/04 |
| 1321481 | 6/1973 | United Kingdom | B44D 1/094 |

OTHER PUBLICATIONS

Patent Abstracts of Japan—vol. 14, No. 90 (C–0791), Feb. 20, 1990 & JP, A, 01 301847 (Komatsu), Dec. 6, 1989.

Patent Abstracts of Japan—vol. 18, No. 97 (C–1167), Feb. 17, 1994 & JP, A, 05 295123 (Japan Synthetic Rubber), Nov. 9, 1993.

Patent Abstracts of Japan—vol. 11, No. 330 (M–636), Oct. 28, 1987 & JP, A, 62 112704 (Toyo Soda Mfg), May 23, 1987.

*Primary Examiner*—H. Thi Le
*Attorney, Agent, or Firm*—Ware, Fressola, Van Der Sluys & Adolphson LLP

[57] ABSTRACT

A high temperature thermal sprayable material, such as a metal or metal oxide, is adhered to the surface of a thermal sprayable plastic particle to form a cladding layer thereon. The high temperature material cladding layer provides a thermal barrier that allows use of the plastic in a high temperature thermal spray process to create a duplex coating containing plastic.

11 Claims, 4 Drawing Sheets

CLAD PLASTIC PARTICLES SUITABLE FOR THERMAL SPRAYING

TECHNICAL FIELD

The present invention relates to the treatment of plastic powder particles to make them suitable for thermal spray processing to form coatings on the surface of substrates. More particularly, the present invention relates to plastic powder particles having a thermal barrier cladding or coating thereon to prevent decomposition of the plastic powder when sprayed in a high temperature thermal spray process, and the method for making such particles.

BACKGROUND OF THE INVENTION

One well known technique for coating surfaces with metal, ceramic or plastic is a thermal spray process. Generally, thermal spray processes typically involve the step of heat softening a heat fusible material such as a metal or ceramic followed by the step of propelling the heat softened material in particulate form against a surface that is to be coated with the heat softened material. The heat softened material and the surface form a bond. Thermal spraying can be accomplished with a flame spray gun that normally uses a combustion or plasma flame to effect melting of a powder. Other heating means such as electric arcs, resistant heaters or induction heaters can also be used, alone or in combination.

Thus, thermal spraying of metallic, ceramic or plastic powders on a surface is a useful process for imparting desired properties to a surface. For example, thermal sprayable molybdenum-iron alloy powders, as described in U.S. Pat. No. 5,292,382, are thermal sprayed on metal surfaces to improve wear resistance, such as sliding wear and/or fretting wear. Mineral coatings are thermal sprayed on plastic surfaces, as described in U.S. Pat. No. 4,388,373, to provide such surfaces with greater hardness and wear resistance. In other well known thermal spray processes, metallic and/or ceramic materials are thermal sprayed to make dimensional restorations to a worn surface, to provide corrosion resistance, or to improve its thermal conductivity. Also, plastics may be applied to a metal surface with a thermal spraying process to provide a metal surface with properties such as improved release, a low coefficient of friction, and non-wetting.

Metal or ceramic thermal sprayable powders typically have high melting points (for metals, around 2600° F., and for ceramics, about 3000° F.), and accordingly, they must be sprayed with high temperature gas streams, such as plasma sprays or acetylene gas, to transfer sufficient heat to melt them. In contrast to metallic or ceramic powders thermally sprayed plastic powders usually having lower melting points (from approximately 180° F. to around 500° F.), and therefore, such powders are usually thermal sprayed with low temperature gas streams, such as, hydrogen or natural gas, to prevent super heating and oxidation thereof.

In some coating applications, it is desirable to combine relatively low melting point plastic materials with relatively high melting point metallic or ceramic thermal sprayable materials to impart the particular properties of each material to a surface simultaneously as a duplex coating in a single application. However, the thermal spraying of such a combination usually provides poor and unacceptable end results because the melting points of the metal and plastic materials are incompatible. For example, the conditions needed to properly melt high melting point thermal spray powders, such as metal powder, will usually cause decomposition and loss of the plastic powder, thus preventing simultaneous deposition of a duplex coating containing both the high melting point metal with the low melting point plastic dispersed through out. On the other hand, if conditions are selected so as to properly melt the plastic powder but prevent decomposition thereof, then the high temperature metal powder will not melt, and accordingly, will not deposit on metal surfaces to form desired duplex coatings.

Surfaces requiring such duplex coatings to provide long wearing release or non-stick properties include rolls used in the paper producing or converting industry. In the past, coatings having metallic and plastic constituents have been applied to such rolls using a two step process wherein a roll is first thermal sprayed with a wear resistant and/or a corrosion resistant metal coating, such as a molybdenum-iron alloy, and then impregnated with a liquified plastic powder, such as PTFE. As those skilled in the art will appreciate, this prior art two step process is cumbersome, costly and difficult to accomplish on site as compared to the present invention. The prior art two step process has limited effectiveness even when applied over a good thermal spray coating, because such thermal spray coatings do not always have the required interconnected porosity to allow effective penetration of the plastic. Thus, the application of plastic to a roll with this two step prior art process usually only results in a surface effect that quickly wears away leaving the roll without the desired release properties imparted by the plastic. If adaptations in the prior art process are made so as to form a higher porosity metal that can absorb more plastic to provide a roll with durable release properties, the resulting matrix properties of the coating tend to be severely reduced. The reduction in matrix properties of such coatings can lead to surfaces that wear and/or corrode rapidly.

As those skilled in the art will appreciate, it is highly desirable to have the ability to control the amount of plastic and high temperature material deposited, as well as the ability to control the time and manner of application, on the surface of a substrate to provide the surface with a duplex coating having long wearing release or non-stick properties. However, this goal is nearly impossible with the prior art two step process.

DISCLOSURE OF THE INVENTION

The present invention is designed to overcome the limitations of the prior art described above, and toward this end, it contemplates a thermal sprayable plastic powder particle having a high temperature cladding material thereon. The cladding applied to the plastic powder particle makes the particle suitable for thermal spraying under conditions that would otherwise cause its decomposition because the cladding acts as a thermal barrier. According to the present invention, the cladding may comprise a single layer of high temperature material or multiple layers of high temperature materials.

A single cladding layer on the plastic powder particle is obtained by at least performing the following steps: substantially surrounding a thermal sprayable plastic powder particle with a high temperature cladding material, heating the plastic powder particle and the surrounding cladding material to the softening temperature of the plastic powder particle, and holding the temperature at the softening temperature for a period of time so as to ensure that the cladding material bonds with the softened plastic powder particle. The particle may then be cooled for later use or used immediately, as further described below, in a thermal spray process.

Additional layers of the same high temperature material, or multiple layers of different high temperature materials may also be clad onto the clad plastic powder particle. If a thermal sprayable plastic particle with multiple cladding layers is desired, the present invention contemplates, in addition to the steps described above for obtaining a clad plastic particle, the additional steps of: cooling the clad particle, and bonding another high temperature material to the cladding layer on the plastic powder particle with an organic binder.

Generally, the cladding parameters, such as the number and thickness of cladding layers, as well as the type of cladding material used, are selected on the basis of formulating a clad thermal sprayable plastic powder particle that will be compatible with the process parameters of a high temperature thermal spray process, other thermal sprayable materials blended therewith, and the desired surface properties of the substrate. According to the present invention, once plastic powder particles are clad with a high temperature material, they may be sprayed directly on the surface of a substrate under high temperature thermal spray conditions or they may be blended with high temperature materials to form a high temperature thermal spray powder blend. Whether the clad plastic powder particles are sprayed directly or blended, the cladding allows the plastic powder particles to be applied with a high temperature thermal spray process because the cladding allows adequate heating and softening of the plastic powder while preventing its decomposition.

Accordingly, it is one object of the present invention to provide a method for controlling the deposition of plastic powders on substrate surfaces using high temperature thermal spray processes.

Other objects and advantages of the present invention will become more apparent to those skilled in the art from the following detailed description and figures illustrating this invention.

BRIEF DESCRIPTION OF THE DRAWINGS

The drawings, not drawn to scale, include.

BEST MODE FOR CARRYING OUT THE INVENTION

Figure 1:
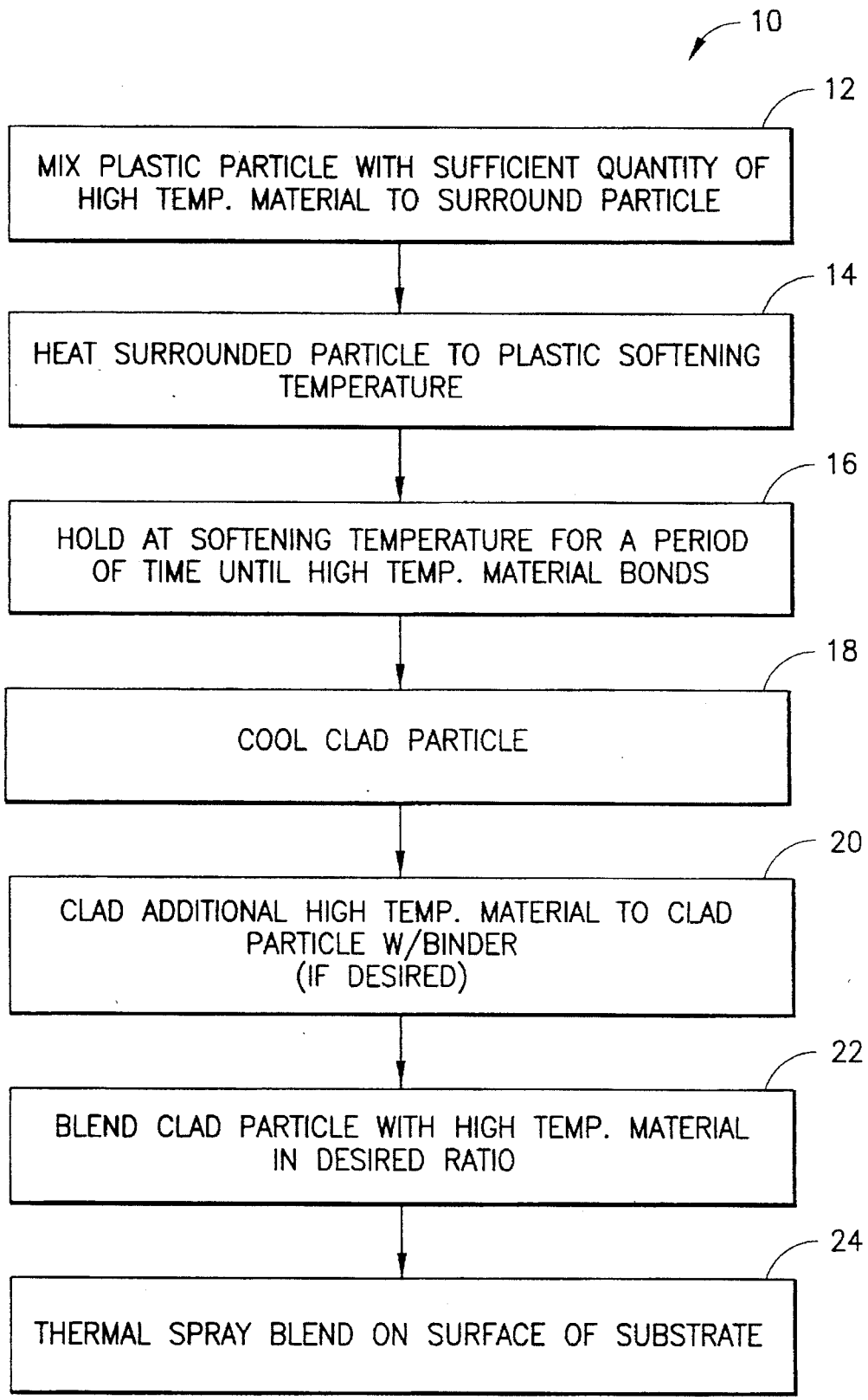
FIG. 1 is a flow diagram of the method for making a thermal sprayable clad plastic powder particle as well as a method for applying a duplex coating to a surface according to the present invention.

FIG. 1 is flow chart 10 of steps comprising a method for applying a duplex coating on a substrate surface containing plastic dispersed throughout a high temperature material, such as metal or ceramic. The exemplary method shown in FIG. 1 includes the basic steps 12, 14 and 16 to provide a cladding layer on the thermal sprayable plastic powder particle to make the plastic powder particles suitable for use in high temperature thermal spray applications, and includes additional steps 18 through 22 to apply additional cladding layers to the thermal sprayable plastic powder particles, and step 24 for coating the surface of a substrate by thermal spray.

According to the present invention, a clad plastic powder particle suitable for use in a high temperature thermal spray process may be formed, as shown by step 12, by mixing plastic powder particles, such as PTFE, sized between 1 μm and 90 μm, for example, with a sufficient quantity of titania powder (typically less than 1 μm in diameter) to substantially cover the surface of the plastic powder particle. It has been found that mixing approximately 80 weight percent PTFE with approximately 20 weight percent titania powder provides sufficient coverage of titania over the surface of the PTFE particles.

Although PTFE is used as an representative thermal sprayable plastic powder in step 12, it should be appreciated that the present invention may be practiced with other fluoropolymer powders such as polytetrafluoroethylene (PTFE), ethyltetrafluoroethylene (ETFE), tetraflouroethylene (TFE), flourinated ethylenepropylene copolymer (FEP), chlorofluoroethylenes, chlorotrifluoroethylenes, fluorohydrocarbons. The present invention may also be practiced with other non-fluoropolymer powder materials such as polyamides, polyvinyl chlorides, epoxys, polyimides and polyesters having desirable non-stick properties.

After the mixing step 12, the PTFE/titania blend is heated in step 14 to approximately 450° F., and held, as shown in step 16 at 450° F. for approximately 30 minutes. This time and temperature has been found to be sufficient to soften at least the surface of the PTFE particles so that the fine titania particles in closest contact with PTFE will bond thereto. The softening temperature of a plastic particle is usually a temperature close to, but below the melting point of the plastic. Because the entire softened PTFE surface is substantially in contact with titania particles, the surface is coated with a layer of titania particles about one titania particle thick (approximately less than 1 μm). The step of heating the PTFE/titania blend 14 to soften the PTFE surface is one of the most important steps of the press because it overcomes the tight bonding of PTFE molecules that essentially make PTFE, and other fluoropolymer materials, almost inert materials. In other words, but for the heat softening step 14, titania, or any other high temperature material, would not adhere to the PTFE surface.

Once a cladding has been placed on the heat softened FIFE surface of a particle, the resulting clad particle may be directly used in a high temperature thermal spray process, if desired, or additional cladding layers may be applied. Or, it may be cooled for later use. If additional cladding layers are to be applied, the titania clad particle is cooled, in step 18, to room temperature. Once cooled, the titania clad particle is ready for further cladding with the same or another high temperature material, such as alumina particles. The cooling step 18 is necessary because the organic binders used to bind alumina particles, as further described below, would otherwise vaporize if applied to a relatively hot clad plastic particle.

For example, the cladding of alumina particles to a titania clad PTFE particle, step 20, as first disclosed herein, involves the application of well known techniques for cladding thermal sprayable materials together using organic binders. See, for example, U.S. Pat. No. 3,655,425, wherein a process using organic binders is disclosed for bonding various thermal sprayable materials together. To obtain a cladding layer of alumina particles on the clad PTFE particles, a sufficient quantity of alumina is mixed with the clad PTFE so as to surround the clad PTFE particles and an organic binder, such as phenolic varnish, is added to the mixture to bind the alumina to the cladding layer.

Figure 2:
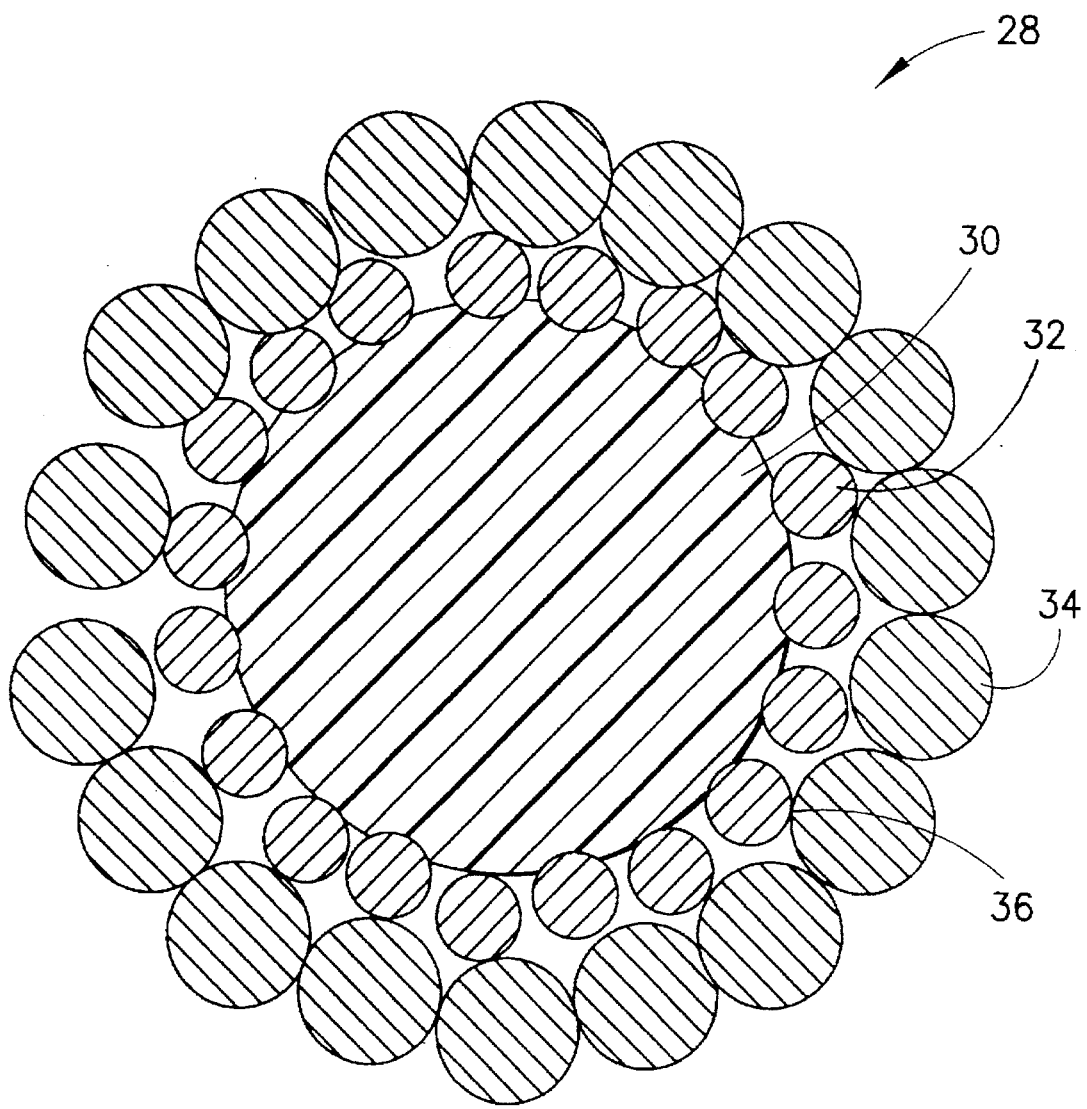
FIG. 2 is a cross-sectional illustration of a thermal sprayable clad plastic powder particle made according to the method shown in FIG. 1.

FIG. 2 is powder particular view of a clad thermal sprayable plastic powder particle made according to process steps 12 through 20 of FIG. 1. According to the process example provided above, the cladding steps result in a clad thermal sprayable plastic powder particle 28 having a plastic core 30, such as a fluoropolymer or fluoro plastic, that is surrounded by an intermediate layer of 20 weight percent titania 32 and an outer layer of 20 weight percent alumina 34. There is an organic binder 36 at the interface of the titania particles 32 and alumina particles 34, and also at the interface of adjacent alumina particles 34. Because the titania and alumina particles 32 and 34, that form the intermediate and outer layers, have much higher melting points than the plastic core 30 therein, the intermediate and outer layers act as a thermal barrier for the lower melting point plastic core 30 when the clad particle 28 is subjected to high temperature conditions in a high temperature thermal spray process.

Without departing from the scope of the present invention, those skilled in the art will recognize that many variations can be made to the cladding on the plastic powder particles, such as variations in material type, number of materials forming layers, and weight percentages thereof. For example, an intermediate layer may be formed with titania and alumina, rather than just titania, by mixing the plastic powder particles with an admixture of titania and alumina. Also, multiple intermixed cladding layers of titania and alumina, for example, may be obtained by mixing an excess amount (amount greater than needed to cover the surface of the FIFE particles) of titania and alumina particles with PTFE particles, heating the mixture to the softening temperature (approximately 450° F.) of the PTFE so that titania and alumina adhere to the PTFE, cooling the titania/alumina clad PTFE particles mixed with the remaining non-adhered titania and alumina, adding an organic binder to the mixture of titania/alumina clad PTFE particles, titania and alumina so as to adhere additional titania and alumina to the titania/alumina clad PTFE particles.

With respect to the selection of cladding material, the present invention contemplates that any high temperature ceramic or metal material can be applied as cladding on the thermal sprayable plastic powder particles by at least following steps 12 though 16 described above. Such cladding materials include metals, metal oxides, metal nitrides, metal chlorides, metal sulfates, metal carbides and, metal alloys and mixtures thereof. Typically, the material selected for cladding on the thermal sprayable plastic powder particles is based on the cladding material's compatibility with the substrate to which the clad plastic powder is to be applied or with the material to which the clad plastic powder is to be mixed. For instance, if the substrate surface or the high temperature thermal spray material is alumina, then the plastic powder particles 30 could be clad with alumina or titania or both. If the substrate to be coated is stainless steel, one may choose a nickel or perhaps cobalt clad on the plastic.

As mentioned above, once the clad plastic powder 30 particles have been formed, they may be applied directly to a substrate surface in a high temperature thermal spray process or they may be blended with another high temperature thermal sprayable material to form a high temperature thermal sprayable powder blend as shown in step 22 in FIG. 1. In situations where the clad plastic powder particles 30 are to be mixed with high temperature thermal sprayable materials to form a high temperature thermal spray powder blend, the quantity of clad thermal sprayable plastic particles 30 used in the blend can be varied so as to control the degree of non-stick or coefficient of friction properties ultimately desired at the surface of a substrate to be treated.

Also, as those skilled in the art will readily appreciate, the quantity and type of high temperature thermal sprayable material blended with the clad plastic particles 30 is selected based on the properties of the substrate that are in need of improvement or change. For example, ceramic materials may be used to improve wear resistance, high alloy materials may be selected to improve corrosion resistance, and aluminum or copper materials may be selected to improve or modify thermal conductivity. Thus, by careful blending of high temperature thermal sprayable materials and clad thermal sprayable plastic powder particles, those skilled in the art will appreciate that controlling the deposit of a duplex coating material on a substrate that has the appropriate release and wear properties, is possible with the present invention.

The invention will be further described in the following illustrative examples wherein all parts are by weight unless otherwise expressed.

EXAMPLE 1

80 weight percent PTFE particles were blended with 20 weight percent titania particles and heated to 450° F. for approximately 30 minutes to form titania clad PTFE particles. The titania clad PTFE particles were cooled and further clad with alumina using organic binders to form multiply-clad PTFE particles comprising a plastic core of approximately 60 weight percent PTFE, an inner cladding layer of approximately 20 weight percent titania and an outer cladding layer 20 weight percent alumina. The resulting clad PTFE particles were mixed with a high temperature thermal sprayable powder consisting of 87 weight percent alumina and 13 weight percent titania in a ratio of approximately 30 weight percent clad PTFE particles to approximately 70 weight percent high temperature thermal sprayable powder. The mixture was applied to a carbon steel substrate using a thermal spray process with a Metco 7MB plasma flame gun employing the following parameters:

2 powder port

GH nozzle;

Argon primary gas at 100 psi (14.5 kPa) and 80 cubic feet/hr flow;

Hydrogen secondary gas at 50 psi (7.25 Kpa) and 15 cubic feet/hr flow;

500 amps, 75 volts, 37.5 kw;.

sprayed at the rate of 6 lbs/hr (2.72 kg/hr);

spray distance of 4 inches (10.16 cm); and

PSA air cooler set at 50 psi (7.25 Kpa) crossed at 6 inches (15.24 cm).

Figure 3:
FIG. 3 is a photograph of the cross-section of a duplex coated substrate, magnified 100 times, after having been treated with a thermal spray powder blend containing: (a) 30 weight percent of a clad plastic powder particles comprising 60 weight percent particle PTFE clad with an inner cladding layer of approximately 20 weight percent $TiO_2$ and an outer cladding layer of approximately 20 weight percent $Al_2O_3$ and (b) 70 weight percent of a high temperature powder comprising 87 weight percent alumina and 13 weight percent titania according to the methods of the present invention.

The resulting coating is shown in FIG. 3. The coating shown therein was sectioned and prepared metallographically to study inclusion and distribution of PTFE. As FIG. 3 shows, the cross-section shows particles of PTFE dispersed through out a continuous matrix of 87% alumina-13% titania. Coating hardness was measured on a Rockwell hardness tester and found to have a hardness of approximately Rc 55. Coatings having the morphology and hardness of the cross-section shown in FIG. 3 have been tested in the pulp and paper industry on rolls requiring special wear and release properties for manufacturing of recycled paper.

EXAMPLE 2

Figure 4:
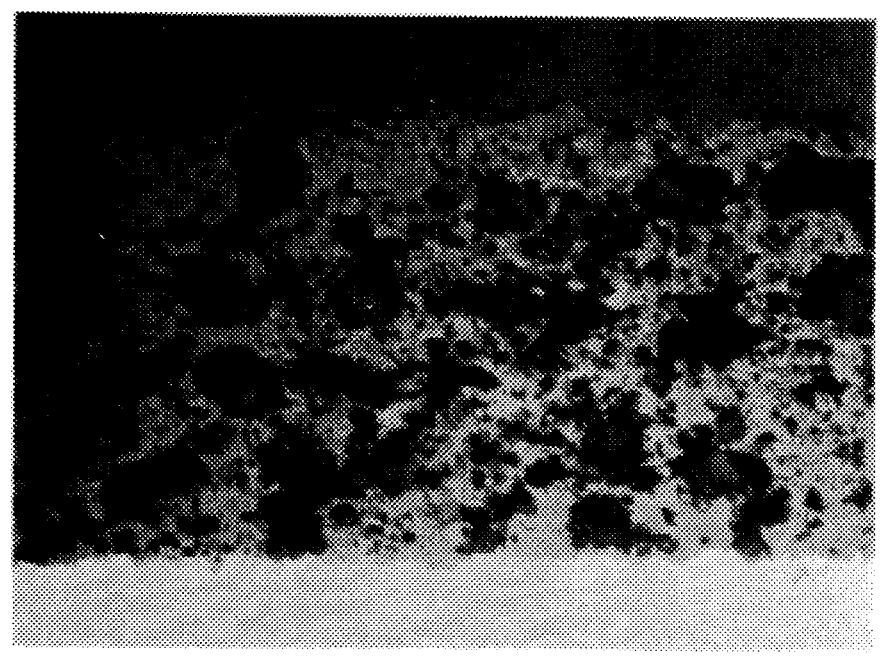
FIG. 4 is a photograph of the cross-section of a coated substrate, magnified 100 times, after having been treated with a thermal spray powder comprising 20 weight percent of clad ETFE (Ethyl-Tetra-Fluoro-Ethylene) particles in FIG. 3 blended with 80 weight percent of the same high temperature powder.

80 weight percent-ETFE particles were blended with 20 weight percent titania particles and heated to 450° F. for approximately 30 minutes to form titania clad ETFE particles. The titania clad ETFE particles were cooled and further clad with alumina using organic binders to form multiply cladded ETFE particles comprising a plastic core of approximately 60 weight percent ETFE, an inner cladding layer of approximately 20 weight percent titania and an outer cladding layer 20 weight percent alumina. The resulting clad ETFE particles were mixed with a high temperature thermal sprayable powder consisting of 87 weight percent alumina and 13 weight percent titania in a ratio of approximately 20 weight percent dad ETFE particles to approximately 80 weight percent high temperature thermal sprayable powder. The mixture was applied under the same thermal spray conditions recited in Example 1. The resulting coating is shown in FIG. 4. The coating shown therein was sectioned and prepared metallographically to study inclusion and distribution of ETFE. As FIG. 4 shows, the cross-section shows particles of ETFE dispersed through out a continuous matrix of 87% alumina-13% titania but there is lower concentration of ETFE in this coating than in the coating shown in FIG. 3.

EXAMPLE 3

Figure 5:
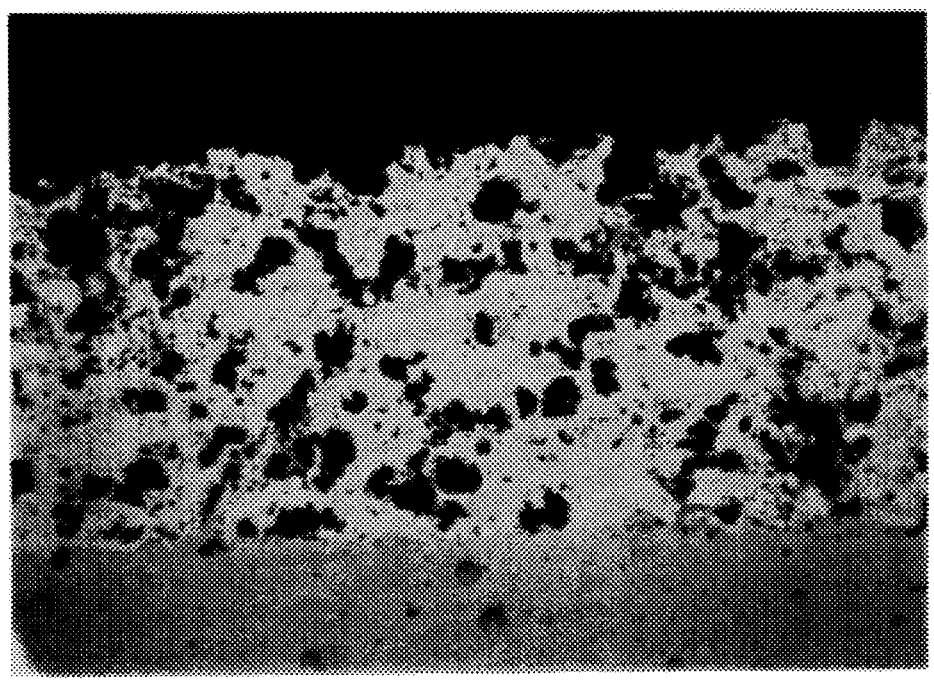
FIG. 5 is a photograph of the cross-section of a coated substrate, magnified 50 times, after having been treated with a thermal spray powder blend containing: (a) 10 weight percent clad plastic powder comprising 60 weight percent ETFE clad with two layers, each 20 weight percent, of $TiO_2$ powder in two steps and (b) 90 weight percent aluminum bronze powder.

80 weight percent ETFE particles were blended with 20 weight percent titania particles and heated to 450° F. for approximately 30 minutes to form titania clad ETFE particles. The titania clad ETFE particles were cooled and further clad another 20 weight percent titania particles using an organic binder to form multiply cladded ETFE particles comprising a plastic core of approximately 60 weight percent ETFE, an inner cladding layer of approximately 20 weight percent titania and an outer cladding layer 20 weight percent titania. The resulting clad ETFE particles were mixed with a high temperature aluminum bronze metal thermal sprayable powder in a ratio of approximately 10 weight percent clad ETFE particles to approximately 90 weight percent aluminum. Coatings on a carbon steel substrate were formed under the same thermal spray conditions set forth in Example 1. The resulting coating is shown in FIG. 5 which is a photograph of the coating's cross-section, magnified 50 times. The cross section shown in FIG. 5 shows ETFE (dark areas) dispersed through out the bronze matrix (light areas). The measured hardness of the coating was $R_{15}y$ 70. This coating could be used, for example, as a low friction surface for the lands of extrusion screws.

EXAMPLE 4

80 weight percent PTFE powder sized between 15 μm and 44 μm was treated with 20 weight percent titania according to the method steps 12 through 16. The treated powder was cooled and screened to obtain 15 μm to 53 μm particles. The resulting titania clad PTFE particles were further clad with 80 weight percent molybdenum particles using an organic binder to hold the molybdenum to the titania. The resulting multiply-clad particles were screened to obtain particle size between 30 μm and 90 μm. These particles were directly plasma sprayed under conditions described in Example 1 to deposit a duplex coating. The resulting dense molybdenum/titania matrix provides wear resistance while the dispersed PTFE therein provides substantially reduced coefficient of friction. This coating is an outstanding candidate for guide rails and machine ways.

It is contemplated that useful coatings can be applied with the present invention to a wide variety of things such as prosthetic devices, bearings, valves, self-lubricating surfaces, ships, conveyor chain guides, among other things. While the applications for such coatings is virtually endless, it will be appreciated that the instant specification and examples are set forth by way of illustration and not limitation, and that various modifications and changes may be made without departing from the spirit and scope of the present invention.

What is claimed is:

1. A particle for depositing a coating on a substrate surface by a thermal spray process, the particle comprising:

a plastic core; and a particulate cladding material, selected from the group consisting of ceramics and metals having a higher melting point than the plastic core, wherein the particulate cladding material is adhered to the plastic core and wherein the particulate cladding material forms a substantially continuous, thermally protective cladding layer around the plastic core to reduce premature melting and vaporization of the plastic core.

2. The particle of claim 1, wherein the plastic forming the plastic core is a fluoropolymer.

3. The particle of claim 1, wherein the plastic forming the plastic core is a fluoropolymer selected from the group consisting of polychlorofluoroethylenes, polychlorotrifluoroethylenes, and polyfluorohydrocarbons.

4. The particle of claim 1, wherein the plastic forming the plastic core is selected from the group consisting of polyamides, polyvinyl chlorides, epoxy resin, polyimides and polyesters.

5. The particle of claim 1, wherein the cladding material is selected from the group consisting of metals, metal alloys, metal oxides, metal nitrides, metal carbides and mixtures thereof.

6. The particle of claim 1, wherein the plastic core is a polytetrafluoroethyelne particle approximately 1 μm to 90 μm in size and wherein the cladding layer is formed from titania particles approximately less than 1 μm in size.

7. A particle for depositing a coating on a substrate surface by a thermal spray process, the particle comprising:

a plastic core;

a first particulate cladding material, selected from the group consisting of ceramics and metals having a higher melting point than the plastic core, wherein the first particulate cladding material is adhered to the plastic core and wherein the first particulate cladding materials forms a substantially continuous, thermally protective intermediate cladding layer to reduce premature melting and vaporization of the plastic core; and a second particulate cladding material, selected from the group consisting of ceramics and metals having a higher melting point than the plastic core, wherein the second particulate cladding material is bonded to the first particulate cladding material with an organic binder to form an outer cladding layer.

8. The particle of claim 7, wherein the plastic forming the plastic core is a fluoropolymer.

9. The particle of claim 7, wherein the plastic forming the plastic core is a fluoropolymer selected from the group consisting of polychlorofluoroethylenes, polychlorotrifluoroethylenes, and polyfluorohydrocarbons.

10. The particle of claim 7, wherein the plastic forming the plastic core is selected from the group consisting of polyamides, polyvinyl chlorides, epoxys, polyimides and polyesters.

11. The particle of claim 7, wherein the plastic core clad with the first particulate cladding adhered thereto is approximately 15 μm to 53 μm in size.

* * * * *